United States Patent [19]

Rowlands et al.

[11] Patent Number: 4,547,507
[45] Date of Patent: Oct. 15, 1985

[54] BENZOTHIOPYRANOPYRIDINONES

[75] Inventors: David A. Rowlands, Malmesbury; Roger J. Gillespie, Swindon; Ian R. Ager, Ashton Keynes; Stephen Clements-Jewery; Colin R. Gardner, both of Swindon, all of England

[73] Assignee: Roussel Uclaf, Paris, France

[21] Appl. No.: 512,964

[22] Filed: Jul. 12, 1983

[30] Foreign Application Priority Data

Jul. 14, 1982 [GB] United Kingdom ............... 8220433

[51] Int. Cl.[4] ............... C07D 513/14; C07D 513/22; A61K 31/38
[52] U.S. Cl. ............... 514/291; 514/285; 546/62; 546/80
[58] Field of Search ............... 546/62, 80, 101; 424/256; 514/291, 285

[56] References Cited

U.S. PATENT DOCUMENTS 3,086,972  4/1963  Jucker et al. ............... 546/80 X
3,236,854  2/1966  Sceaux et al. ............... 546/80

FOREIGN PATENT DOCUMENTS 47-30198  7/1972  Japan ............... 546/62
47-30199  7/1972  Japan ............... 546/62

*Primary Examiner*—Joseph Paul Brust
*Attorney, Agent, or Firm*—Bierman, Peroff & Muserlian

[57] ABSTRACT

Novel benzothiopyranopyridinones of the formula

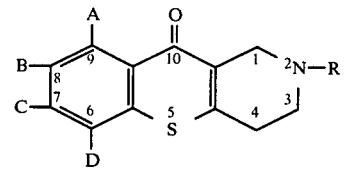

wherein A,B,C and D are individually selected from the group consisting of hydrogen, alkyl and alkoxy of 1 to 6 carbon atoms, nitro, halogen, amino and acylamino of 2 to 7 carbon atoms or A and B or C and D taken with the carbon atoms to which they are attached form a benzene ring, R is selected from the group consisting of hydrogen and R', R' is selected from the group consisting of alkyl of 1 to 9 carbon atoms, alkenyl of 2 to 9 carbon atoms optionally substituted with an —OH, cycloalkyl of 3 to 9 carbon atoms, phenyl, aralkyl of 7 to 9 carbon atoms and —$(CH_2)_n$—Z, n is an integer from 1 to 4, Z is selected from the group consisting of cycloalkyl and cycloalkenyl of 3 to 9 carbon atoms, dioxanyl, 2-oxobenzimidazolyl, benzoyl, halo substituted benzoyl, cyano, alkoxy carbonyl of 2 to 7 carbon atoms and carbamoyl and their non-toxic, pharmaceutically acceptable acid addition salts having antipsychotic and antidepressant and antidopaminergic activity.

27 Claims, No Drawings

BENZOTHIOPYRANOPYRIDINONES

OBJECTS OF THE INVENTION

It is an object of the invention to provide the novel compounds of formula I and their non-toxic, pharmaceutically acceptable acid addition salts and a process for their preparation.

It is another object of the invention to provide novel antipsychotic and antidepressant compositions and to a novel method treating psychosis and depression in warm-blooded animals.

It is a further object of the invention to provide novel antidopaminergic compositions and to a novel method of inducing antidopaminergic activity in warm-blooded animals.

These and other objects and advantages of the invention will become obvious from the following detailed description.

THE INVENTION

The novel compounds of the invention are selected from the group consisting of benzothiopyranopyridinones of the formula

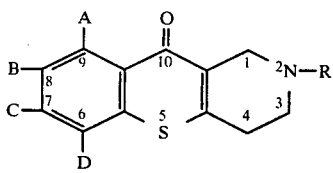

wherein A,B,C and D are individually selected from the group consisting of hydrogen, alkyl and alkoxy of 1 to 6 carbon atoms, nitro, halogen, amino and acylamino of 2 to 7 carbon atoms or A and B or C and D taken with the carbon atoms to which they are attached form a benzene ring, R is selected from the group consisting of hydrogen and R', R' is selected from the group consisting of alkyl of 1 to 9 carbon atoms, alkenyl of 2 to 9 carbon atoms optionally substituted with an —OH, cycloalkyl of 3 to 9 carbon atoms, phenyl, aralkyl of 7 to 9 carbon atoms and —$(CH_2)_n$—Z, n is an integer from 1 to 4, Z is selected from the group consisting of cycloalkyl and cycloalkenyl of 3 to 9 carbon atoms, dioxanyl, 2-oxobenzimidazolyl, benzoyl, halo substituted benzoyl, cyano, alkoxy carbonyl of 2 to 7 carbon atoms and carbamoyl and their non-toxic, pharmaceutically acceptable acid addition salts.

Examples of alkyl of 1 to 6 carbon atoms are methyl, ethyl, propyl, isopropyl, butyl and pentyl and examples of alkoxy of 1 to 6 carbon atoms are methoxy, ethoxy, propoxy, isopropoxy, butoxy and pentoxy. Examples of acylamino of 2 to 7 carbon atoms are acetamido, propionamido and butyrylamido and examples of halogen are fluorine, chlorine and bromine.

Examples of alkyl of 1 to 9 carbon atoms are methyl, ethyl, n-propyl, isopropyl, n-butyl, isobutyl, n-pentyl, isopentyl, hexyl, heptyl and nonyl; examples of alkenyl of 2 to 9 carbon atoms are vinyl, allyl and examples of cycloalkyl or cycloalkenyl of 3 to 9 carbon atoms are cyclopropyl, cyclobutyl, cyclopentyl cyclohexyl, cycloheptyl, cyclobutenyl, cyclopentenyl or cycloexenyl; examples of aralkyl of 7 to 9 carbon atoms are benzyl, phenethyl and phenylpropyl. Examples of —$(CH_2)_n$—Z are those where Z is benzoyl or halo substituted benzoyl such as phenyl-4-oxo-butyl, phenyl-3-oxo-propyl, phenyl-2-oxoethyl or p-fluorophenyl-4-oxo-butyl. Examples of alkoxycarbonyl of 2 to 7 carbon atoms are methoxycarbonyl, ethoxycarbonyl, propoxycarbonyl or butoxycarbonyl.

Examples of suitable acids to form the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzene sulfonic acid.

Examples of preferred compounds of formula I are those wherein A is hydrogen, those wherein B is hydrogen, methyl, methoxy, nitro, chlorine, fluorine or acetamido, those wherein A and B together with the carbon atoms to which they are attached form a benzene ring, those wherein C is hydrogen or methoxy, those wherein D is hydrogen and C and D together with the carbon atoms to which they are attached form a benzene ring but not when A and B form a benzene ring and their non-toxic, pharmaceutically acceptable acid addition salts.

Also preferred compounds of formula I are those wherein R is hydrogen or R' and R' is alkyl of 1 to 9 carbon atoms, benzyl, cyclohexylmethyl, 4-(p-fluorophenyl)-4-oxobutyl or ethoxycarbonylethyl and their non-toxic, pharmaceutically acceptable acid addition salts. Especially preferred are the compounds of formula I wherein A,B,C and D are all hydrogen.

Examples of specific preferred compounds of formula I are selected from the group consisting of 2-cyclohexylmethyl-1,2,3,4-tetrahydro-10H-(1)-benzothiopyrano[3,2-c]pyridin-10-one, 1,2,3,4-tetrahydro-2-n-propyl-10H-(1)-benzothiopyrano[3,2-c]pyridin-10-one, 2-n-butyl-1,2,3,4-tetrahydro-10H-(1)-benzothiopyrano[3,2-c]pyridin-10-one, 1,2,3,4-tetrahydro-2-isopentyl-10H-(1)-benzothiopyrano[3,2-c]pyridin-10-one, 1,2,3,4-tetrahydro-2-n-pentyl-10H-(1)-benzothiopyrano[3,2-c]pyridin-10-one, 2-(4-p-fluorophenyl-4-oxobutyl)-1,2,3,4-tetrahydro-10H-(1)-benzothiopyrano[3,2-c]pyridin-10-one, 2-cyclohexylmethyl-8-fluoro-1,2,3,4-tetrahydro-10H-(1)-benzothiopyrano[3,2-c]pyridin-10-one, 2-cyclopropylmethyl-1,2,3,4-tetrahydro-10H-(1)-benzothiopyrano[3,2-c]pyridin-10-one, 2-cyclobutylmethyl-1,2,3,4-tetrahydro-10H-(1)-benzothiopyrano[3,2-c]pyridin-10-one and 2-cyclopentylmethyl-1,2,3,4-tetrahydro-10H-(1)-benzothiopyrano[3,2-c]pyridin-10-one and their non-toxic, pharmaceutically acceptable acid addition salts.

The novel process of the invention for the preparation of the compounds of formula I comprises reacting a compounds of the formula

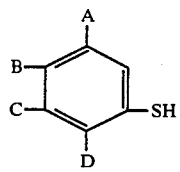

wherein A,B,C and D have the above definitions with a compound of the formula

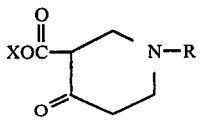

wherein R has the above definition and X is alkyl of 1 to 8 carbon atoms to obtain a compound of formula I which may be recovered as the free base or may be salified to obtain its non-toxic, pharmaceutically acceptable acid addition salts or the compounds of formula I wherein R is hydrogen are reacted with a compound of the formula Hal—R'   IV wherein Hal is chlorine, bromine or iodine and R' has the above definition other then phenyl to obtain a compound of the formula

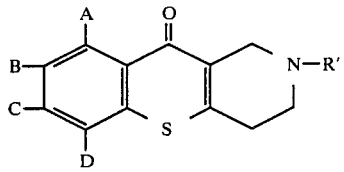

which may be recovered as the free base or may be salified to its non-toxic, pharmaceutically acceptable acid addition salts or reacting a compound of formula I wherein R is hydrogen with a compound of the formula $CH_2=CH-Z'$   V wherein Z' is cyano, carbamoyl or alkoxycarbonyl of 2 to 7 carbon atoms to obtain a compound of the formula

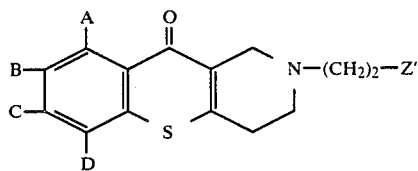

which may be recovered as such or in the form of its acid addition salts.

Preferably, the reaction of the compounds of formulae II and III is effected by warming them for several hours up to several days in the presence of a strong acid such as polyphosphoric acid and the preferred acid addition salt is the hydrochloride.

Preferably, the reaction of the compound of the formula I wherein R is hydrogen and the compound of formula IV is effected in the presence of an alcohol such as ethanol at the reflux temperature and in the presence of an amine base such as triethylamine. The said reaction may also be carried out in the presence of a solvent such as dimethylformamide at elevated temperature in the presence of potassium iodide and an alkali metal carbonate such as potassium carbonate.

The reaction of a compound of formula I wherein R is hydrogen and a compound of formula V is preferably effected in the presence of an alcohol such as ethanol at the reflux temperature. The acid addition salts are preferably formed by reacting substantially stoichiometric amounts of acid and base with or without isolation of the free base.

The compounds of formula III wherein R is hydrogen are known and those compounds of formula III wherein R is other than hydrogen may be prepared by cyclization of a compound of the formula

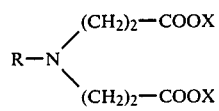

wherein R is as defined above other than hydrogen and X has the above definition, preferably by reaction with sodium hydride in a solvent such as toluene in the presence of traces of an alcohol such as ethanol with heating to distill off solvent and alcohols.

The compounds of formula VI can be prepared by reacting an amine of the formula R—$NH_2$ with two equivalents of an acrylate of the formula $CH_2=CH-COOX$   VII with heating in a solvent such as ethanol or other alcohol.

The novel antipsychotic and antidepressant compositions of the invention are comprised of an antidepressantly and antipsychotically effective amount of at least one compound of formula I and/or their non-toxic, pharmaceutically acceptable acid addition salts and an inert pharmaceutical carrier.

The novel antidopaminergic compositions of the invention are comprised of an antidopaminergically effective amount of at least one compound of formula I and/or their non-toxic, pharmaceutically acceptable acid addition salts and an inert pharmaceutical carrier.

The compositions may be in the form of tablets, dragees, gelatin capsules, granules, suppositories, syrups, aerosols and injectable solutions or suspensions prepared in a known manner. Examples of suitable excipients are talc, arabic gum, starch, lactose, magnesium stearate, cacao butter, aqueous and non-aqueous vehicles, animal and vegetable fats, paraffin derivatives, glycols, various wetting agents, dispersants and emulsifiers and preservatives.

The compositions of the invention have very interesting pharmacological properties, notably their joint dopamine and $\alpha_2$ receptor antagonist properties, but generally low affinity for $\alpha_1$ and muscarinic receptors. Such compounds possess antipsychotic and antidepressant activity with a minimum of autonomic or extrapyramidal side effects and these properties are illustrated by radioreceptor assay test results given hereinafter. The compositions are useful, for example, in methods of antidopaminergic, antipsychotic and antidepressant therapy. They are useful for the treatment of neurovegetative unequilibrium and character and behavior problems.

The novel method of the invention for inducing antipsychotic, antidepressant or antidopaminergic activity in warm-blooded animals, including humans, comprises administering to warm-blooded animals an amount of at least one compound of formula I and/or its non-toxic, pharmaceutically acceptable acid addition salts in an amount sufficient to induce antipsychotic, antidepressant or antidopaminergic activity. The compounds may be administered orally, rectally or parenterally. The novel daily dose 0,004 to 14 mg/kg depending on the specific condition treated, the specific compound and the method of the administration. Oral administration is usually 0,004 to 5 mg/kg daily.

In the following examples there are described several preferred examples to illustrate the invention. However, it is to be understood that the invention is not intended to be limited to the specific embodiments.

EXAMPLE 1

1,2,3,4-tetrahydro-10H-(1)-benzothiopyrano[3,2-c]pyridin-10-one hydrochloride—Method A 2.33 g of methyl 4-oxo-3-pyridinecarboxylate hydrochloride and 1.1 ml of thiophenol were slowly added at 100° C. with stirring to 35 g of polyphosphoric acid and the mixture was stirred at 100° C. for 4 hours and was then poured into 500 ml of water. The pH of the mixture was adjusted to 8 by addition of sodium bicarbonate and the mixture was extracted with chloroform three times. The organic phase was washed with water, dried over magnesium sulfate and filtered and the filtrate was evaporated to dryness under reduced pressure. The residue was dissolved in a small amount of chloroform and the solution was acidified with a solution of hydrogen chloride in ether. Additional ether was added and the mixture was filtered. The product was crystallized from aqueous methanol and dried over $P_2O_5$ to obtain 1.365 g (54% yield) of 1,2,3,4-tetrahydro-10H-(1)-benzothiopyrano[3,2-c]pyridin-10-one hydrochloride melting at 270°–272° C. (decomp.)

EXAMPLES 2 TO 10

Using the procedure of Example 1, the appropriate compounds of formulae II and III were reacted to form the following compounds of formula I with the yields and IR spectra reported in Table I and melting point and analysis of Table II. The compounds so prepared were as follows:

EXAMPLE 2

1,2,3,4-tetrahydro-8-methyl-10H-(1)benzothiopyrano[3,2-c]pyridin-10-one hydrochloride.

EXAMPLE 3

1,2,3,4-tetrahydro-7-methoxy-10H-(1)-benzothiopyrano[3,2-c]pyridin-10-one hydrochloride.

EXAMPLE 4

1,2,3,4-tetrahydro-8-methoxy-10H-(1)-benzothiopyrano[3,2-c]pyridin-10-one hydrochloride.

EXAMPLE 5

1,2,3,4-tetrahydro-12H-naphtho[1',2':5,6]thiopyrano[3,2-c]pyridin-12-one hydrochloride.

EXAMPLE 6

2-benzyl-1,2,3,4-tetrahydro-10H-(1)-benzothiopyrano[3,2-c]pyridin-10-one hydrochloride.

EXAMPLE 7

8-chloro-1,2,3,4-tetrahydro-10H-(1)-benzothiopyrano[3,2-c]pyridin-10-one hydrochloride.

EXAMPLE 8

1,2,3,4-tetrahydro-12H-naphtho[1',2':6,5]thiopyrano[3,2-c]pyridin-12-one hydrochloride.

EXAMPLE 9

1,2,3,4-tetrahydro-8-nitro-10H-(1)-benzothiopyrano[3,2-c]pyridin-10-one hydrochloride.

EXAMPLE 10

8-acetamido-1,2,3,4-tetrahydro-10H-(1)-benzothiopyrano[3,2-c]pyridin-10-one hydrochloride.

EXAMPLE 11

1,2,3,4-tetrahydro-2-n-propyl-10H-(1)-benzothiopyrano[3,2-c]pyridin-10-one hydrochloride—Method $B_1$ A solution of 1.44 ml of n-propyl iodide in 10 ml of ethanol was added dropwise over 20 minutes to a refluxing solution of 2.50 g of 1,2,3,4-tetrahydro-10H-(1)-benzothiopyrano[3,2-c]pyridine-10-one hydrochloride, 3.5 ml of triethylamine in 10 ml of ethanol. The mixture was refluxed for four hours after which thin layer chromatography ($SiO_2:CH_2Cl_2$ with 10% methanol) showed no starting material. The solution was evaporated to dryness and the residue was partitioned between chloroform and dilute aqueous hydrogen chloride. The aqueous layer was adjusted to a pH of 8 by addition of sodium carbonate and was extracted three times with chloroform. The organic phase was washed with water, dried over magnesium sulfate and evaporated to dryness under reduced pressure. The residue was chromatographed over silica gel and eluted with methylene dichloride containing 1% of ethanol. The product was dissolved in chloroform and the solution was acidified by addition of ether saturated with hydrogen chloride. More ether was added and the mixture was filtered. The product was crystallized from ethanol and dried under reduced pressure to obtain 1.75 g (60% yield) of 1,2,3,4-tetrahydro-2-n-propyl-10H-(1)-benzothiopyrano[3,2-c]pyridin-10-one hydrochloride melting at 218° to 221° C.

EXAMPLES 12 TO 18

Using the procedure of Example 11, the appropriate compounds of formulae I and IV were reacted to obtain the following compounds of formula I with the yields and IR spectra of Table I and the melting points and analysis of Table II. The compounds so prepared were as follows:

EXAMPLE 12

1,2,3,4-tetrahydro-2-methyl-10H-(1)-benzothiopyrano[3,2-c]pyridin-10-one hydrochloride.

EXAMPLE 13

2-ethyl-1,2,3,4-tetrahydro-10H-(1)-benzothiopyrano[3,2-c]pyridin-10-one hydrochloride.

EXAMPLE 14

2-n-butyl-1,2,3,4-tetrahydro-10H-(1)-benzothiopyrano[3,2-c]pyridin-10-one hydrochloride.

EXAMPLE 15

1,2,3,4-tetrahydro-2-isopentyl-10H-(1)-benzothiopyrano[3,2-c]pyridin-10-one hydrochloride.

EXAMPLE 16

2-(4-p-fluorophenyl-4-oxobutyl)-1,2,3,4-tetrahydro-10H-(1)-benzothiopyrano-[3,2-c]pyridin-10-one hydrochloride.

EXAMPLE 17

1,2,3,4-tetrahydro-2-n-pentyl-10H-(1)-benzothiopyrano[3,2-c]pyridin-10-one hydrochloride.

EXAMPLE 18

2-n-hexyl-1,2,3,4-tetrahydro-10H-(1)-benzothiopyrano[3,2-c]pyridin-10-one hydrochloride.

EXAMPLE 19

1,2,3,4-tetrahydro-2-isobutyl-10H-(1)-benzothiopyrano[3,2-c]pyridin-10-one hydrochloride—Method $B_2$ A solution of 1.58 ml of isobutyl bromide in 10 ml of dimethylformamide was added over 30 minutes at 100° C. to a stirred mixture of 2.46 g of 1,2,3,4-tetrahydro-10H-(1)-benzothiopyrano[3,2-c]pyridin-10-one hydrochloride, 2.81 g of anhydrous potassium carbonate, 0.1 g of potassium iodide and 100 ml of dimethylformamide and the mixture was stirred at 100° C. for 6 hours and was then poured into 500 ml of water. The mixture was extracted three times with ethyl acetate and the organic phase was evaporated to a small volume and acidified with hydrogen chloride in ether. More ether was added and the mixture was filtered. The product was crystallized from ethanol and was dried under reduced pressure over $P_2O_5$ to obtain 1.32 (44% yield) of 1,2,3,4-tetrahydro-2-isobutyl-10H-(1)-benzothiopyrano[3,2-c]pyridin-10-one hydrochloride melting at 202°–203° C. (decomp.).

EXAMPLE 20

Using the procedure of Example 19, 1,2,3,4-tetrahydro-10H-(1)-benzothiopyrano[3,2-c]pyridin-10-one hydrochloride and bromomethylcyclohexane were reacted to obtain 2-cyclohexylmethyl-1,2,3,4-tetrahydro-10H-(1)-benzothiopyrano[3,2-c]pyridin-10-one hydrochloride with the melting point and analysis of Table II.

EXAMPLE 21

2-(2-ethoxycarbonylethyl)-1,2,3,4-tetrahydro-10H-(1)-benzothiopyrano[3,2-c]pyridin-10-one hydrochloride—Method C A mixture of 2.0 g of 1,2,3,4-tetrahydro-10H-(1)-benzothiopyrano[3,2-c]pyridin-10-one, 0.95 ml of ethyl acrylate and 60 ml of ethanol was refluxed for 20 hours and was evaporated to dryness under reduced pressure. The oil residue was dissolved in methylene dichloride and the solution was acidified by addition of ether saturated with hydrogen chloride. More ether was added and the mixture was filtered. The product was crystallized from ethanol and dried under reduced pressure to obtain 1.54 g (55% yield) of 2-(2-ethoxycarbonylethyl)-1,2,3,4-tetrahydro-10H-(1)-benzothiopyrano[3,2-c]pyridin-10-one hydrochloride—Method C melting at 190°–192.5° C. (decomp.).

EXAMPLE 22

Using the procedure of Example 21, 1,2,3,4-tetrahydro-10H-(1)-benzothiopyrano[3,2-c]pyridin-10-one and cyanoethenyl were reacted to obtain 2-(2-cyanoethyl)-1,2,3,4-tetrahydro-10H-(1)-benzothiopyrano[3,2-c]pyridin-10-one hydrochloride with the melting point and analysis of Table II and the yield and IR spectrum of Table I.

EXAMPLE 23

Using the procedure of Example 21, 1,2,3,4-tetrahydro-10H-(1)-benzothiopyrano[3,2-c]pyridin-10-one and carbamoylethenyl were reacted to obtain 2-(2-carbamoylethyl)-1,2,3,4-tetrahydro-10H-(1)-benzothiopyrano[3,2-c]pyridin-10-one hydrochloride with the yield and IR spectrum of Table I and the melting point and analysis of Table II.

TABLE I

| Example | A | B | C | D | R | Method of synthesis | Yield (%) | Recryst. solvent | IR (cm$^{-1}$) KBr |
|---|---|---|---|---|---|---|---|---|---|
| 1 | H | H | H | H | H, HCl | A | 55 | MeOH/H$_2$O | 3420br, 2800br, 1610, 1590, 1440, 1395, 1180, 1080, 1020, 740. |
| 2 | H | Me | H | H | H, HCl | A | 65 | MeOH | 3440br, 2750br, 1620, 1600, 1415, 1335, 1105, 825, 765. |
| 3 | H | H | OMe | H | H, HCl | A | 61 | MeOH/H$_2$O | 3430br, 2740br, 1615, 1595, 1420, 1240, 1035, 850, 760. |
| 4 | H | OMe | H | H | H, HCl | A | 58 | MeOH | 3520br, 2740br, 1600br, 1485, 1425, 1220, 1125, 825, 765. |
| 5 | 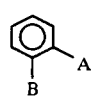 | | H | H | H, HCl | A | 59 | MeOH | 3500br, 2760br, 1595br, 1423, 1395, 1120, 820, 795, 745. |
| 6 | H | H | H | H |  | A | 53 | EtOH/H$_2$O | 3410br, 2390br, 1620, 1595, 1440, 1380, 745. |
| 7 | H | Cl | H | H | H, HCl | A | 43 | MeOH/H$_2$O | 3450br, 2750br, 1610, 1590, 1415, 1330, 1095, 825, 765. |
| 8 | H | H |  | | H, HCl | A | 60 | MeOH/H$_2$O | 3400br, 2800br, 1605, 1580, 1400, 1190, 820, 760. |
| 9 | H | NO$_2$ | H | H | H, HCl | A | 10 | EtOH/H$_2$O | 3500br, 2960, 1625, 1610, 1530, 1345, 738. |
| 10 | H | NHAC | H | H | H, HCl | A | | MeOH/H$_2$O | |
| 11 | H | H | H | H | CH$_2$CH$_2$CH$_3$, HCl | B$_1$ | 60 | EtOH | 3450br, 2470br, 1625, 1595, 1440, |

TABLE I-continued

| Example | A | B | C | D | R | Method of synthesis | Yield (%) | Recryst. solvent | IR (cm$^{-1}$) KBr |
|---|---|---|---|---|---|---|---|---|---|
| 12 | H | H | H | H | CH$_3$, HCl | B$_1$ | 37 | EtOH | 1385, 1330, 985, 795, 740. 3500br, 2500br, 1620, 1580br, 1480, 1435, 1395, 1330, 1195, 1080, 995, 820, 790, 745, 730. |
| 13 | H | H | H | H | CH$_2$CH$_3$, HCl | B$_1$ | 52 | EtOH | 3400br, 2500br, 1615, 1595, 1445, 1325, 740, 735. |
| 14 | H | H | H | H | CH$_2$CH$_2$CH$_2$CH$_3$, HCl | B$_1$ | 43 | EtOH | 3480br, 2500br, 1620, 1595, 1440, 1385, 1325, 740. |
| 15 | H | H | H | H | CH$_2$CH$_2$CH(CH$_3$)$_2$, HCl | B$_1$ | 45 | EtOH | 3450br, 2500br, 1620br, 1390, 1320, 740, 1440. |
| 16 | H | H | H | H | CH$_2$CH$_2$CH$_2$C(O)–C$_6$H$_4$–F, HCl | B$_1$ | 25 | | 3450br, 2440br, 1690, 1600br, 1215, 1155, 975, 740. |
| 17 | H | H | H | H | CH$_2$CH$_2$CH$_2$CH$_2$CH$_3$, HCl | B$_1$ | 51 | EtOH/EtOAC | 3500br, 2500br, 1630, 1600, 1445, 1390, 1330, 950, 745. |
| 18 | H | H | H | H | CH$_2$CH$_2$CH$_2$CH$_2$CH$_2$CH$_3$, HCl | B$_1$ | 57 | EtOH/EtOAC | 3500br, 2950, 2400br, 1630, 1595, 1445br, 1390, 1330, 795, 745. |
| 19 | H | H | H | H | CH$_2$CH(CH$_3$)$_2$, HCl | B$_2$ | 44 | EtOH/H$_2$O | 3500br, 2500br, 1620, 1590, 1440, 1420, 1385, 1325, 980, 735. |
| 20 | H | H | H | H | CH$_2$–C$_6$H$_{11}$, HCl | B$_2$ | 35 | EtOH | 3500br, 2450br, 1630, 1595, 1445, 1385, 1325, 980, 745. |
| 21 | H | H | H | H | CH$_2$CH$_2$CO$_2$Et, HCl | C | 55 | EtOH | 3450br, 2500br, 1745, 1620, 1595, 1445, 1390, 1325, 1200, 1080, 1030, 745. |
| 22 | H | H | H | H | CH$_2$CH$_2$CN, HCl | C | 63 | EtOH/H$_2$O | 3500br, 2460bbr, 2230, 1620, 1595, 14751430br, 1390, 1330, 970, 745. |
| 23 | H | H | H | H | CH$_2$CH$_2$CONH$_2$, HCl | C | 60 | MeOH/H$_2$O | 3350br, 2550br, 1675, 1620, 1590, 1445, 1425, 1400, 1325, 745. |

TABLE II

| Example | Mpt | Formula | M. wt. includ. H$_2$O | Moles H$_2$O | Calculated C | H | N | S | Cl | Found C | H | N | S | Cl |
|---|---|---|---|---|---|---|---|---|---|---|---|---|---|---|
| 1 | 270–272 | C$_{12}$H$_{12}$NOSCl | 253.75 | — | 56.80 | 4.77 | 5.52 | 12.63 | 13.97 | 56.76 | 4.74 | 5.67 | 12.61 | 13.91 |
| 2 | 268–269.5 | C$_{13}$H$_{14}$NOSCl | 267.77 | — | 58.31 | 5.27 | 5.23 | 11.97 | 13.24 | 58.00 | 5.26 | 5.28 | 12.01 | 13.20 |
| 3 | 269–271 | C$_{13}$H$_{14}$NO$_2$SCl | 283.77 | — | 55.02 | 4.97 | 4.94 | 11.30 | 12.49 | 55.08 | 4.94 | 4.92 | 11.45 | 12.5 |
| 4 | 241–242 | C$_{13}$H$_{14}$NO$_2$SCl | 283.77 | — | 55.02 | 4.97 | 4.94 | 11.30 | 12.49 | 54.87 | 5.02 | 4.92 | 11.16 | 12.47 |
| 5 | 226–229 | C$_{16}$H$_{14}$NOSCl | 312.82 | 0.5 | 61.43 | 4.83 | 4.48 | 10.25 | 11.33 | 61.84 | 4.79 | 4.67 | 10.35 | 11.33 |
| 6 | 219–222 | C$_{19}$H$_{18}$NOSCl | 343.87 | — | 66.37 | 5.28 | 4.07 | 9.32 | 10.31 | 66.31 | 5.31 | 3.95 | 9.29 | 10.29 |
| 7 | 281–285 | C$_{12}$H$_{11}$NOSCl$_2$ | 297.21 | 0.5 | 48.49 | 4.07 | 4.71 | 10.79 | 23.86 | 48.55 | 4.02 | 4.74 | 10.93 | 23.91 |
| 8 | 245–248 | C$_{16}$H$_{14}$NOSCl | 321..83 | 1.0 | 59.71 | 5.01 | 4.35 | 9.96 | 11.02 | 60.04 | 5.04 | 4.48 | 10.00 | 11.25 |
| 9 | | C$_{12}$H$_{11}$N$_2$O$_3$SCl | | | | | | | | | | | | |
| 10 | | C$_{14}$H$_{15}$N$_2$O$_2$SCl | | | | | | | | | | | | |
| 11 | 218–221 | C$_{15}$H$_{18}$NOSCl | 295.83 | — | 60.90 | 6.13 | 4.74 | 10.84 | 11.98 | 60.60 | 6.09 | 4.69 | 10.67 | 11.99 |
| 12 | 237–238 | C$_{13}$—H$_{14}$NOSCl | 276.78 | 0.5 | 56.41 | 5.46 | 5.06 | 11.58 | 12.81 | 56.41 | 5.45 | 5.17 | 11.70 | 13.02 |
| 13 | 221–224 | C$_{14}$H$_{16}$NOSCl | 281.81 | — | 59.67 | 5.72 | 4.97 | 11.38 | 12.58 | 59.57 | 5.70 | 5.01 | 11.53 | 12.70 |
| 14 | 209–211 | C$_{16}$H$_{20}$NOSCl | 318.87 | 0.5 | 60.27 | 6.64 | 4.39 | 10.05 | 11.12 | 60.45 | 6.62 | 4.24 | 10.29 | 11.10 |
| 15 | 196–199 | C$_{17}$H$_{22}$NOSCl | 328.39 | 0.25 | 62.18 | 6.91 | 4.27 | 9.76 | 10.80 | 62.13 | 6.85 | 4.19 | 9.73 | 10.83 |
| 16 | 236–239 | C$_{22}$H$_{21}$NO$_2$SClF | | | | | | | | | | | | |
| 17 | 182–185 | C$_{17}$H$_{22}$NOSCl | 328.39 | 0.25 | 62.18 | 6.91 | 4.27 | 9.76 | 10.80 | 62.17 | 6.90 | 4.21 | 9.70 | 10.92 |
| 18 | 175–177 | C$_{18}$H$_{24}$NOSCl | 324.42 | 0.25 | 63.14 | 7.21 | 4.09 | 9.36 | 10.35 | 63.48 | 7.15 | 4.03 | 9.35 | 10.39 |
| 19 | 202–203 | C$_{16}$H$_{20}$NOSCl | 309.86 | — | 62.02 | 6.51 | 4.52 | 10.35 | 11.44 | 61.71 | 6.45 | 4.52 | 10.56 | 11.50 |
| 20 | 171–173 | C$_{19}$H$_{24}$NOSCl | 349.92 | — | 65.22 | 6.91 | 4.00 | 9.16 | 10.13 | 64.92 | 6.79 | 4.00 | 9.31 | 10.28 |
| 21 | 190–192.5 | C$_{17}$H$_{20}$NO$_3$SCl | 367.39 | 0.75 | 55.58 | 5.90 | 3.81 | 8.73 | 9.65 | 55.54 | 5.87 | 3.79 | 9.18 | 9.85 |
| 22 | 247–252 | C$_{15}$H$_{15}$N$_2$OSCl | 306.81 | — | 58.72 | 4.93 | 9.13 | 10.45 | 11.55 | 58.89 | 4.95 | 9.13 | 10.49 | 11.66 |
| 23 | 249–253 | C$_{15}$H$_{17}$N$_2$O$_2$SCl | 324.83 | — | 55.47 | 5.28 | 8.62 | 9.87 | 10.91 | 55.23 | 5.29 | 8.48 | 9.89 | 10.96 |

EXAMPLE 24

2-cyclohexylmethyl-8-fluoro-1,2,3,4-tetrahydro-10H-(1)-benzothiopyrano[3,2-c]pyridin-10-one hydrochloride

STEP A: Diethyl 3,3'-cyclohexylmethylamino-bispropionate 57.7 g of ethyl acrylate were slowly added to a solution of 21.75 g of cyclohexylmethylamine and 100 ml of ethanol and the mixture was refluxed for 20 hours and evaporated to dryness under reduced pressure. The oil residue was distilled under reduced pressure to obtain 50.4 g (84% yield) of diethyl 3,3'-cyclohexylmethylamino-bispropionate in the form of colorless oil with a boiling point of 154° to 156° C. at 0.5 mm Hg.

STEP B: Ethyl 1-cyclohexylmethyl-4-oxo-piperidine-3-carboxylate hydrochloride 5 g of 80% sodium hydride were added with stirring under nitrogen to a solution of 39 g of the product of Step A in 250 ml of toluene followed by the addition of a few drops of ethanol resulting in vigorous effervescence followed by the formation of a thick white paste. The mixture was gently heated to distill off ethanol and toluene until the distillate reached 110° C. (about 30 minutes) and the mixture was cooled to room temperature. 15 ml of concentrated hydrochloric acid were slowly added thereto with stirring and then a minimum volume of water was added thereto to dissolve the solid sodium chloride. The decanted aqueous phase was extracted with 100 ml of ether and the combined organic extracts were washed with 25 ml of water, dried over magnesium sulfate and a solution of 10% of hydrogen chloride in 50 ml of ethanol was added to the organic phase. The mixture was filtered and the product was washed with ether and dried to obtain 25 g (66% yield) of ethyl 1-cyclohexylmethyl-4-oxo-piperidine-3-carboxylate hydrochloride melting at 153° C.

STEP C: 2-cyclohexylmethyl-8-fluoro-1,2,3,4-tetrahydro-10H-(1)-benzothiopyrano[3,2-c]pyridin-10-one hydrochloride A mixture of 6.68 g of the product of Step B and 2.51 g of p-fluoro-thiophenol were added in two portions with stirring over 20 minutes to 80 g of polyphosphoric acid heated to 100° to 120° C. and the mixture was held at 110° C. for two hours to form a yellow solution which was poured into 500 ml of water. The resulting suspension was adjusted to a pH of 8 by addition of sodium carbonate and the yellow precipitate formed was recovered by filtration. The product was washed with water and dissolved in 250 ml of dichloromethane. The solution was washed with water, dried over magnesium sulfate and evaporated to dryness under reduced pressure. The residue was dissolved in a mixture of ethyl acetate and ethanol and 10 ml of a solution of 10% hydrogen chloride in ethanol were added thereto. The mixture was filtered and the pale cream colored product was washed with a little ethanol and dried under reduced pressure to obtain 2.73 g (39% yield) of 2-cyclohexylmethyl-8-fluoro-1,2,3,4-tetrahydro-10H-(1)-benzothiopyrano[3,2-c]pyridin-10-one hydrochloride melting at 243° C. (decomp.).

Analysis: $C_{19}H_{23}NOSClF$: Calculated: %C 62.03, %H 6.30, %N 3.81, %Cl 9.64, %S 8.71, %F 5.16. Found: %C 61.75, %H 6.37, %N 3.74, %Cl 9.83, %S 8.72, %F 5.07.

EXAMPLES 25 TO 37

Using procedure B of Examples 11 or 19, the appropriate compounds of formula I reported in Table III were prepared for Examples 25 to 36 and the compound of Example 37 was prepared by the process of Example 24. The melting point and analysis are reported in Table III.

TABLE III

| Ex No. | R | | m. pt. | Analysis Calc. | | | | | Analysis Found | | | | |
|---|---|---|---|---|---|---|---|---|---|---|---|---|---|
| | | | | C | H | N | Cl | S | C | H | N | Cl | S |
| 25 | cyclopropylmethyl | HCl·0.33 H₂O | 257° (dec) | 61.24 | 5.99 | 4.46 | 11.30 | 10.21 | 61.11 | 6.02 | 4.37 | 11.33 | 10.21 |
| 26 | cyclobutylmethyl | HCl | 244 (dec) | 63.44 | 6.26 | 4.35 | 11.01 | 9.96 | 63.19 | 6.24 | 4.27 | 10.97 | 9.85 |
| 27 | cyclopentylmethyl | HCl | 240 (dec) | | | | | | | | | | |
| 28 | cycloheptylmethyl | HCl | 241 (dec) | 65.20 | 7.25 | 3.80 | 9.62 | 8.70 | 65.32 | 7.22 | 3.78 | 9.81 | 8.88 |
| 29 | cyclohexenylmethyl | HCl | 256 (dec) | 65.59 | 6.38 | 4.03 | 10.19 | 9.22 | 64.96 | 6.35 | 4.01 | 10.35 | 9.17 |
| 30 | cyclohexylethyl | free base | 115° | 73.35 | 7.69 | 4.28 | — | 9.79 | 73.49 | 7.69 | 4.21 | — | 9.81 |
| 31 | 1,3-dioxan-2-ylethyl | free base | 99° | 65.23 | 6.39 | 4.23 | — | 9.67 | 65.20 | 6.37 | 4.24 | — | 9.80 |

TABLE III-continued

| Ex No. | R | | m. pt. | Calc. C | Calc. H | Calc. N | Calc. Cl | Calc. S | Found C | Found H | Found N | Found Cl | Found S |
|---|---|---|---|---|---|---|---|---|---|---|---|---|---|
| 32 | —CH₂CH₂CH₂Ph | HCl | 238 (dec) | 65.47 | 5.77 | 3.82 | 9.66 | 8.74 | 65.85 | 5.72 | 3.84 | 10.01 | 8.93 |
| 33 | —CH₂CH₂C(O)Ph | HCl | 255 (dec) | 64.60 | 4.88 | 3.77 | 9.53 | 8.62 | 64.37 | 4.96 | 3.71 | 9.51 | 8.57 |
| 34 | —CH₂CH₂CH=CH₂ | HCl·0.25 H₂O | 257 (dec) | 60.39 | 5.58 | 4.70 | 11.88 | 10.75 | 60.41 | 5.65 | 4.59 | 11.87 | 10.63 |
| 35 | —CH₂CH₂CH₂OH | HCl·0.25 H₂O | 239° | 55.62 | 5.50 | 4.63 | 11.73 | 10.60 | 55.74 | 5.49 | 4.53 | 11.63 | 10.60 |
| 36 | —(CH₂)₄—N(benzimidazolon-1-yl) | HCl 0.5 H₂O | 265° (dec) | 60.47 | 5.30 | 9.62 | 8.11 | 7.34 | 60.69 | 5.37 | 9.62 | 8.27 | 7.30 |
| 37 | —CH₂-cyclohexyl | HCl | 243° (dec) | 64.86 | 6.60 | 4.17 | 10.55 | 9.54 | 64.13 | 6.64 | 4.09 | 10.63 | 9.34 |

EXAMPLE 38

Using the procedure of Example 24 and replacing the p-fluoro-thiophenol with p-methoxy-thiophenol, there was obtained 2-cyclohexylmethyl-8-methoxy-1,2,3,4-tetrahydro-10H-(1)-benzothiopyrano[3,2-c]pyridin-10-one hydrochloride melting at 231° C. (decomp.).

Analysis: $C_{20}H_{26}NClSO_2$: Calculated: %C 63.22, %H 6.90, %N 3.69, %Cl 9.33, %S 8.44. Found: %C 63.03, %H 6.91, %N 3.64, %Cl 9.43, %S 8.51.

IR Spectrum (KBr-disc): absorption at 2920 cm$^{-1}$, 2840 cm$^{-1}$, 2300–2600 cm$^{-1}$ and 1690 cm$^{1}$.

| NMR Spectrum (deuterochloroform): free base | | | |
|---|---|---|---|
| 2.1 | 1H | d (J = 2.5 Hz) | H₉ |
| 2.67 | 1H | d (J = 9 Hz) | H₆ |
| 2.9 | 1H | dd (J = 2.5 and 9 Hz) | H₇ |
| 6.14 | 3H | s | OMe |
| 6.48 | 2H | bs | 2 × H |
| 7.37 | 4H | bs | 2 × (H₃ + H₄) |
| 7.65 | 2H | bd (J = 6 Hz) | N—CH₂ |
| 7.9–9.5 | 11H | m | cyclohexyl |

EXAMPLE 39

Tablets were prepared containing 25 mg of either the compound of Example 16 or of Example 20 and sufficient excipient of lactose, starch, talc and magnesium stearate for a tablet weighing 150 mg.

PHARMACOLOGICAL DATA

Test A—[³H Spiroperidol displacement from rat striatal dopamine receptor binding sites (a) Radioligand—[phenyl-4-(n)-³H]Spiroperido (Amersham International, TRK 570, 21 Ci/mmol was used as a 1 μCi/1 μl solution in ethanol and this solution was diluted to 250 μCi in 1 ml of ethanol to produce a stock solution. This stock solution was diluted 3.2/10,000 in assay buffer and 0.1 ml volumes of this were added to 2 ml binding assays =0.19 nM [³H]spiroperidol and =0.08 μCi/binding assay (b) Assay buffer—The assay buffer was a modified 50 mM Tris HCl buffer with a pH of 7.6 containing the following additions: NaCl-120 mM, KCl-5 mM, MgCl₂-1 mM, CaCl₂-2 mM, Pargyline-10 μM and 1-Ascorbic Acid-0.1%

(c) Membrane preparation—The striata were dissected from male CFHB rats and homogenized in 20 volumes of ice cold 0.32M sucrose with a Teflon/glass homogenizer and the homogenate was centrifuged at 1000 g for 10 minutes. The resulting supernatant was recentrifuged at 30,000 g for 30 minutes and the supernatant was discarded and the pellet was resuspended by homogenization in 30 volumes of ice cold assay buffer.

(d) Non-specific binding—Non-specific binding was accounted for by the inclusion of 1 μM(+)butaclamol in blank binding assays which required a stock solution of 20 μM in distilled water.

(e) Displacing compounds—Solutions were prepared at 20x final assay concentration in distilled water.

(f) Binding assay protocol—1.3 ml assay buffer, 0.5 ml membrane suspension, 0.1 ml distilled H₂O or drug solution and 0.1 ml [³H]spiroperidol dilution Binding assays were made up in ice with the [³H]spiroperidol being added last and incubated at 37° C. for 10 minutes. The bound ligand was separated by filtration through Whatman GF/C filters under vacuum followed by 2×10 ml rinses of ice cold assay buffer. The filters were dried at 80° C. and counted in 5 ml volumes of ECONOFLUOR (NEN) scintillation cocktail. All binding assays, controls, blanks and each of four displacer concentration were run in triplicate. IC₅₀ values (Test A) were obtained graphically from log dose versus percent inhibition of specific binding plots.

Test B—[³H]Pyrazosin displacement from rat cortical α₁ receptor binding sites (a) Radioligand—[³H]Prazosin (Amersham International, TRK 647, 28 Ci/mmole) was used as a 1 µCi/1 µl solution and this stock solution was diluted 1/18,000 in assay buffer and 0.1 ml volumes of this were added to 2 ml binding assay. =0.1 nM [³H]Prazosin and =0.0056 µCi/binding assay (b) Membrane preparation—The cerebral cortices were dissected from male CFHB rats and homogenized in 20 volumes of ice cold 0.32M sucrose using a Teflon/glass homogenizer and the homogenate was centrifuged at 1000 g for 10 minutes. The resulting pellet was discarded and the supernatant was recentrifuged at 30,000 g for 30 minutes. The supernatant was discarded and the pellet was resuspended by homogenization in 50 volumes of 50 mM pH 7.5 Tris HCl buffer (assay buffer).

(c) Non-specific binding—Non-specific binding was accounted for by the inclusion of 100 µM 1-noradrenaline in blank binding assays which required a stock solution of 2 mM 1-noradrenaline made up fresh daily in 0.1% 1-ascorbic acid.

(d) Displacing compounds—Solutions were prepared at 20x final assay concentration in distilled water.

(e) Binding assay protocol—1.3 ml assay buffer, 0.5 ml membrane suspension, 0.1 ml distilled H₂O or drug solution and 0.1 ml [³H]pyrazosin dilution Binding assays were made up in ice with the [³H]pyrazosin being added last and incubated at 25° C. for 30 minutes. The bound ligand was separated by filtration through Whatman GF/C glass fibre filters under vacuum followed by 2×10 ml rinses of ice cold assay buffer. The filters were dried at 80° C. and counted in 5 ml volumes of ECONOFLUOR (NEN) scintillation cocktail. All binding assays, controls, blanks and each of four displacer concentrations were run in triplicate. IC₅₀ values (Test B) were obtained graphically from log dose versus percent inhibition of specific binding plots.

Test C—[³H]Dihydroergocryptine displacement from rat cortical α₂*receptor binding sites (a) Radioligand—[9,10(n)-³H]9,10-Dihydroergocryptine (Amersham International, TRK 555, 17.5 Ci/mmole) was used as a 1 µCi/1 µl solution and this stock solution was diluted 1/6250 in assay buffer and 0.1 ml volumes of this were added to 2 ml binding assays. =0.45 nM and =0.016 µCi/binding assay

*In cortical membranes, [³H]dihydroergocryptine binds to both α₁ and α₂ receptor binding sites under the conditions of assay described here, approximately 80% of the binding is associated with α₂ receptors.

(b) Membrane preparation—As for Test B
(c) Non-specific binding—As for Test B
(d) Displacing compounds—As for Test B
(e) Assay protocol—As for Test B with the exception that the binding assays were incubated at 25° C. for 45 minutes in the dark.

Test D—[³H]Quinuclidinyl benzylate displacement from rat cortical muscarinic receptor binding sites (a) Radioligand—DL-[3-³H]Quinuclidinyl benzylate (Amersham International, TRK 506, 12 Ci/mmol) was used as a 1 µCi/1 µl solution and this stock solution was diluted 1/13333 in assay buffer and 0.1 ml volumes of this were added to 2 ml binding assay =0.31 nM and =0.0075 µCi/binding assay (b) Membrane preparation—As for Test B (c) Non-specific binding—Non-specific binding was accounted for by the inclusion of 100 µM oxotremorine sesquifumarate in blank binding assays and this required a stock solution of 2 mM in distilled H₂O.

(d) Displacement compounds—As for Test B (e) Assay protocol—As for Test B with the exception that the binding assays were incubated at 25° C. for 60 minutes.

The test results are reported in the following Table.

TABLE IV

| Example | Test A receptor DA | B α₁ | C α₂ | D MUSC |
|---|---|---|---|---|
| 1 | 6.5 | 6.6 | 0.6 | 32.0 |
| 2 | >10 | >10 | 3.3 | 45.7 |
| 3 | >10 | >10 | 4.3 | 26.9 |
| 4 | >10 | 7.8 | 2.9 | 57.5 |
| 5 | 5.2 | 1.7 | 1.6 | 19.5 |
| 6 | 0.68 | 4.0 | 0.5 | >100 |
| 7 | 5.1 | >10 | 2.2 | 85.1 |
| 8 | 0.68 | 0.74 | 1.0 | 8.1 |
| 11 | 0.49 | 1.3 | 0.15 | >100 |
| 12 | 2.8 | 3.1 | 0.93 | 32.4 |
| 13 | 1.0 | 1.5 | 0.29 | 44.7 |
| 14 | 0.08 | 0.89 | 0.11 | 75.8 |
| 15 | 0.06 | 0.68 | 0.17 | 87.1 |
| 16 | 0.02 | 0.02 | 0.02 | >100 |
| 17 | 0.07 | 0.31 | 0.07 | 39.8 |
| 18 | 0.13 | 0.40 | 0.08 | 15.8 |
| 19 | 0.10 | 4.6 | 0.15 | >100 |
| 20 | 0.01 | 2.7 | 0.23 | >100 |
| 21 | 0.78 | 7.1 | 1.0 | 100 |
| 22 | >10 | >10 | >10 | >100 |
| 23 | 4.2 | 5.9 | 3.0 | >100 |
| 24 | 0.04 | >10 | >10 | >100 |
| 25 | 0.22 | 1.23 | 0.06 | 43.0 |
| 26 | 0.06 | 0.69 | 0.05 | 50.0 |
| 27 | 0.04 | 0.68 | 0.05 | 57.5 |
| 28 | 0.15 | 2.82 | 0.32 | >100 |
| 29 | 0.17 | 2.63 | 0.15 | >100 |
| 30 | 0.18 | 1.15 | 0.19 | >100 |
| 31 | 0.56 | 3.40 | 0.65 | 74.1 |
| 32 | 0.23 | 0.17 | 0.21 | 46.8 |
| 33 | >10 | >10 | >10 | >100 |
| 34 | 2.81 | 3.98 | 0.39 | 37.2 |
| 35 | 10 | 10.0 | 3.30 | 71.0 |
| 36 | 0.03 | 0.19 | 0.15 | 44.7 |
| 37 | 0.16 | 1.59 | 0.60 | 11.7 |
| 38 | 0.76 | >10 | 2.19 | 91.2 |

Various modifications of the products and processes of the invention may be made without departing from the spirit or scope thereof and it should be understood that the invention is intended to be limited only as defined in the appended claims.

What we claim is:

1. A compound selected from the group consisting of benzothiopyranopyridinones of the formula

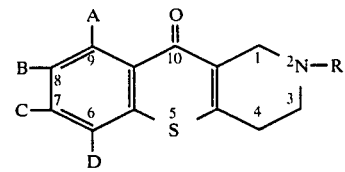

wherein A,B,C and D are individually selected from the group consisting of hydrogen, alkyl and alkoxy of 1 to 6 carbon atoms, nitro, halogen, amino and acylamino of a carboxylic acid of 2 to 7 carbon atoms or A and B or C and D taken with the carbon atoms to which they are attached form a benzene ring, R is selected from the group consisting of hydrogen and R', R' is selected from the group consisting of alkyl of 1 to 9 carbon atoms, alkenyl of 2 to 9 carbon atoms, alkenyl of 2 to 9 carbon atoms substituted with an —OH, cycloalkyl of 3 to 9 carbon atoms, phenyl, phenylalkyl of 7 to 9 carbon atoms and —(CH$_2$)$_n$—Z, n is an integer from 1 to 4, Z is selected from the group consisting of cycloalkyl and cycloalkenyl of 3 to 9 carbon atoms, dioxanyl, 2-oxobenzimidazolyl, benzoyl, halo substituted benzoyl, cyano, alkoxy carbonyl of 2 to 7 carbon atoms and carbamoyl and their non-toxic, pharmaceutically acceptable acid addition salts.

2. A compound of claim 1 wherein A is hydrogen.

3. A compound of claim 1 or 2 wherein B is selected from the group consisting of hydrogen, methyl, methoxy, nitro, chlorine, fluorine and acetamido.

4. A compound of claim 1 wherein A and B together with the carbon atoms to which they are attached form a benzene ring.

5. A compound of claim 1 wherein C is hydrogen or methoxy and D is hydrogen.

6. A compound of claim 1 wherein C and D together with the carbon atoms to which they are attached form a benzene ring and A and B do not form a benzene ring.

7. A compound of claim 1 wherein R is hydrogen or R' and R' is selected from the group consisting of alkyl of 1 to 9 carbon atoms, benzyl, cyclohexylmethyl, 4-(p-fluorophenyl)-4-oxo-butyl and ethoxycarbonylethyl.

8. A compound of claim 1 or 7 wherein A,B,C and D are hydrogen.

9. A compound of claim 1 selected from the group consisting of 2-cyclohexylmethyl-1,2,3,4-tetrahydro-10H-(1)-benzothiopyrano[3,2-c]pyridin-10-one, 1,2,3,4-tetrahydro-2-n-propyl-10H-(1)-benzothiopyrano[3,2-c]pyridin-10-one, 2-n-butyl-1,2,3,4-tetrahydro-10H-(1)-benzothiopyrano[3,2-c]pyridin-10-one, 1,2,3,4-tetrahydro-2-isopentyl-10H-(1)-benzothiopyrano[3,2-c]pyridin-10-one, 1,2,3,4-tetrahydro-2-n-pentyl-10H-(1)-benzothiopyrano[3,2-c]pyridin-10-one, 2-(4-p-fluorophenyl-4-oxobutyl)-1,2,3,4-tetrahydro-10H-(1)-benzothiopyrano[3,2-c]pyridin-10-one, 2-cyclohexylmethyl-8-fluoro-1,2,3,4-tetrahydro-10H-(1)-benzothiopyrano[3,2-c]pyridin-10-one, 2-cyclopropylmethyl-1,2,3,4-tetrahydro-10H-(1)-benzothiopyrano[3,2-c]pyridin-10-one, 2-cyclobutylmethyl-1,2,3,4-tetrahydro-10H-(1)-benzothiopyrano[3,2-c]pyridin-10-one and 2-cyclopentylmethyl-1,2,3,4-tetrahydro-10H-(1)-benzothiopyrano[3,2-c]pyridin-10-one and their non-toxic, pharmaceutically acceptable acid addition salts.

10. An antipychotic and antidepressant composition comprising an antipsychotically and antidepressantly effective amount of at least one compound of claim 1 and an inert pharmaceutical carrier.

11. A composition of claim 10 wherein A is hydrogen.

12. A composition of claim 10 wherein B is selected from the group consisting of hydrogen, methyl, methoxy, nitro, chlorine, fluorine and acetamido.

13. A composition of claim 10 wherein A and B together with the carbon atoms to which they are attached form a benzene ring.

14. A composition of claim 10 wherein C is hydrogen or methoxy and D is hydrogen.

15. A composition of claim 10 wherein C and D together with the carbon atoms to which they are attached form a benzene ring and A and B do not form a benzene ring.

16. A composition of claim 10 wherein R is hydrogen or R' and R' is selected from the group consisting of alkyl of 1 to 9 carbon atoms, benzyl, cyclohexymethyl, 4-(p-fluorophenyl)-4-oxo-butyl and ethoxycarbonylethyl.

17. A composition of claim 10 wherein A,B,C and D are hydrogen.

18. A composition of claim 10 wherein the active compound is selected from the group consisting of 2-cyclohexylmethyl-1,2,3,4-tetrahydro-10H-(1)-benzothiopyrano[3,2-c]pyridin-10-one, 1,2,3,4-tetrahydro-2-n-propyl-10H-(1)-benzothiopyrano[3,2-c]pyridin-10-one, 2-n-butyl-1,2,3,4-tetrahydro-10H-(1)-benzothiopyrano[3,2-c]pyridin-10-one, 1,2,3,4-tetrahydro-2-isopentyl-10H-(1)-benzothiopyrano[3,2-c]pyridin-10-one, 1,2,3,4-tetrahydro-2-n-pentyl-10H-(1)-benzothiopyrano[3,2-c]pyridin-10-one, 2-(4-p-fluorophenyl-4-oxobutyl)-1,2,3,4-tetrahydro-10H-(1)-benzothiopyrano[3,2-c]pyridin-10-one, 2-cyclohexylmethyl-8-fluoro-1,2,3,4-tetrahydro-10H-(1)-benzothiopyrano[3,2-c]pyridin-10-one, 2-cyclopropylmethyl-1,2,3,4-tetrahydro-10H-(1)-benzothiopyrano[3,2-c]pyridin-10-one, 2-cyclobutylmethyl-1,2,3,4-tetrahydro-10H-(1)benzothiopyrano[3,2-c]pyridin-10-one and 2-cyclopentylmethyl-1,2,3,4-tetrahydro-10H-(1)-benzothiopyrano[3,2-c]pyridin-10-one and their non-toxic, pharmaceutically acceptable acid addition salts.

19. A method of inducing antipyschotic, antidepressant or antidopaminergic activity in warm-blooded animals comprising administering to warm-blooded animals an amount of at least one compound of claim 1 sufficient to induce antipsychotic, antidepressant or antidopaminergic activity.

20. A method of claim 19 wherein A is hydrogen.

21. A method of claim 19 wherein B is selected from the group consisting of hydrogen, methyl, methoxy, nitro, chlorine, fluorine and acetamide.

22. A method of claim 19 wherein A and B together with the carbon atoms to which they are attached form a benzene ring.

23. A method of claim 19 wherein C is hydrogen or methoxy and D is hydrogen.

24. A method of claim 19 wherein C and D together with the carbon atoms to which they are attached form a benzene ring and A and B do not form a benzene ring.

25. A method of claim 19 wherein R is hydrogen or R' and R' is selected from the group consisting of alkyl of 1 to 9 carbon atoms, benzyl, cyclohexylmethyl, 4-(p-fluorophenyl)-4-oxo-butyl and ethoxycarbonylethyl.

26. A method of claim 19 wherein A,B,C and D are hydrogen.

27. A method of claim 19 wherein the active compound is selected from the group consisting of 2-cyclohexylmethyl-1,2,3,4-tetrahydro-10H-(1)-benzothiopyrano[3,2-c]pyridin-10-one, 1,2,3,4-tetrahydro-2-n-propyl-10H-(1)-benzothiopyrano[3,2-c]pyridin-10-one, 2-n-butyl-1,2,3,4-tetrahydro-10H-(1)-benzothiopyrano[3,2-c]pyridin-10-one, 1,2,3,4-tetrahydro-2-isopentyl-10H-(1)-benzothiopyrano[3,2-c]pyridin-10-one, 1,2,3,4-tetrahydro-2-n-pentyl-10H-(1)-benzothiopyrano[3,2-c]pyridin-10-one, 2-(4-p-fluorophenyl-4-oxobutyl)-1,2,3,4-tetrahydro-10H-(1)-benzothio[3,2-c]pyridin-10-one, 2-cyclohexylmethyl-8-fluoro-1,2,3,4-tetrahydro-10H-(1)-benzothiopyranol[3,2-c]pyridin-10-one, 2-cyclopropylmethyl-1,2,3,4-tetrahydro-10H-(1)-benzothiopyrano[3,2-c]pyridin-10-one, 2-cyclobutylmethyl-1,2,3,4-tetrahydro-10H-(1)-benzothiopyranol [3,2-c]pyridin-10-one and 2-cyclopentylmethyl-1,2,3,4-tetrahydro-10H-(1)-benzothiopyranol[3,2-c]pyridin-10-one and their non-toxic, pharmaceutically acceptable acid addition salts.

* * * * *